United States Patent [19]
Fletcher et al.

[11] 3,971,363
[45] July 27, 1976

[54] MYOCARDIUM WALL THICKNESS TRANSDUCER AND MEASURING METHOD

[76] Inventors: James C. Fletcher, Administrator of the National Aeronautics and Space Administration, with respect to an invention of Cyril Feldstein, Sierra Madre, Calif.; Gilbert W. Lewis, Arcadia, Calif.; Robert H. Silver, Van Nuys, Calif.; Virgil H. Culler, La Canada, Calif.

[22] Filed: May 5, 1975

[21] Appl. No.: 574,218

[52] U.S. Cl. ............................ 128/2 S; 128/2.05 R; 338/6
[51] Int. Cl.² .......................................... A61B 5/10
[58] Field of Search ............... 128/2 R, 2 S, 2.05 E, 128/2.05 P, 2.05 R; 338/6

[56] References Cited
UNITED STATES PATENTS

| | | | |
|---|---|---|---|
| 2,815,424 | 12/1957 | Painter | 338/6 |
| 3,553,625 | 1/1971 | Stedman | 128/2.05 E UX |
| 3,820,529 | 6/1974 | Gause et al. | 128/2 S |

Primary Examiner—Anton O. Oechsle
Attorney, Agent, or Firm—Monte F. Mott; Wildred Grifka; John R. Manning

[57] ABSTRACT

A myocardium wall thickness measuring transducer comprises a circular beam of high compliance and an elongated spike which extends in the plane in which the beam is disposed. The spike is connected at one point to the beam while a working end of the spike to which a barb is attached, extends through an opening in the beam at a substantially diametrically opposite point. The beam portion, surrounding the opening, is free to move or be displaced relative to the spike. A sensitive strain gauge is bonded to the beam to sense changes in the tension thereof. The working end of the spike is inserted through the epicardium into the myocardium so that the spike and the beam are in a plane substantially perpendicular to the epicardium at the point of insertion. The spike is inserted, to a depth at which a minimal beam deforming force is applied by the myocardium to the beam portion surrounding the opening. As the heart contracts and myocardium thickness increases larger beam-deforming forces are applied to the beam which increase the beam tension, which is sensed by the strain gauge whose changing output is supplied to an appropriate recorder.

10 Claims, 7 Drawing Figures

MYOCARDIUM WALL THICKNESS TRANSDUCER AND MEASURING METHOD

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

The present invention generally relates to a displacement transducer and, more particularly, to a miniature transducer for measuring relative changes in thickness of muscles or the like as myocardium wall thickness.

2. Description of the Prior Art

In medical research, particularly involving animals, it is often necessary to measure changes in muscle thickness such as for example changes in the thickness of the myocardium during a cardiac cycle. To this end two different transducers have been proposed in the prior art. However, both prior art transducers suffer from several very serious disadvantages. Each of the prior art transducers penetrates the entire myocardium and includes one element which is pressed against the endocardium while another element of the transducer is pressed against the epicardium. The insertion of such a transducer can result in traumatizing the animal under study. Also, due to their design they are characterized by low compliance, which in effect loads the myocardium and thereby affects its changes in thickness during a normal cardiac cycle. In addition, their implementation is time consuming and requires highly experienced technicians. Another very significant disadvantage of each prior art transducer is the fact that once implanted in the myocardium of an animal it can only be removed by cutting it out of the myocardium. It cannot be extracted and thereafter implanted in a different location of the myocardium of the same living animal. Another undesirable disadvantage of each prior art transducer is the fact that it can only measure changes in the thickness of the entire myocardium. It cannot be used to measure changes or relative changes of the myocardium thickness as a function of different depths within the myocardium.

OBJECTS AND SUMMARY OF THE INVENTION

It is a primary object of the present invention to provide a new improved miniature transducer for measuring changes in thickness of the myocardium, which does not possess any of the above-described disadvantages of prior art transducers.

Another object of the invention is to provide a new transducer for measuring changes in muscle thickness which is easily implantable without traumatizing the subject, without affecting the normal muscle behavior and which is removable and implantable at a different muscle location.

A further object of the present invention is to provide a new miniature transducer capable of measuring changes or relative changes in myocardium wall thickness as a function of different depths within the myocardium, and which is easily removable for insertion at a different location of the myocardium.

These and other objects are achieved by providing a transducer consisting of a circular beam with a high degree of elastic compliance on which a strain gauge is bonded. The transducer also includes a small arrow-like prong or spike which is connected at one point to the circular beam and extends through an opening at a diametrically opposite point in the beam. In operation the spike is pushed into the myocardium until the portion of the circular beam with the opening, through which the spike extends through the beam, rests firmly on the epicardium, when the myocardium is of smallest thickness, which occurs during heart expansion in the cardiac cycle. Contractions of the myocardium causes its thickness to increase, which in turn, compresses the beam, causing the strain gauge output, which is connected to a conventional recording device, to change. As will be pointed out hereinafter spacers may be used to vary the depth of penetration of the spike into the myocardium thereby enabling the determination of muscle thickness changes for different depths of penetration.

The novel features of the invention are set forth with particularity in the appended claims. The invention will best be understood from the following description when read in conjunction with the accompanying drawings.

DESCRIPTION OF THE PREFERRED EMBODIMENTS

Figure 1:
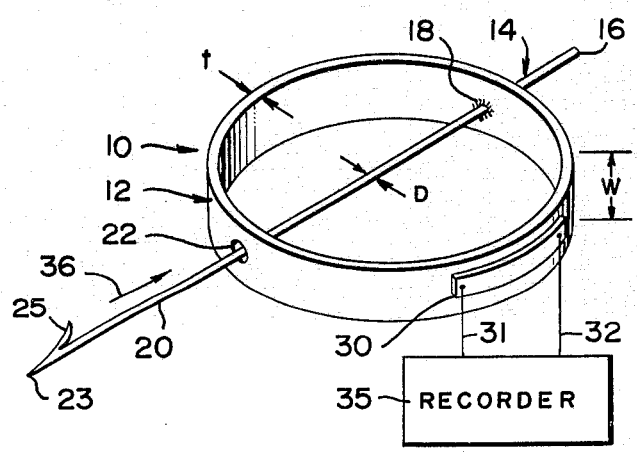
FIG. 1 is a isometric view of one embodiment of the novel transducer of the present invention.

Attention is now directed to FIG. 1 wherein the novel displacement transducer is generally designated by reference numeral 10, and shown comprising a circular beam 12 of high compliance and an arrow-like prong or spike 14, which extends through and beyond opposite sides of the beam 12. The beam width is designated by W while its thickness is designated by $t$ and the spike diameter by D. As shown, $W > D$. The spike has a top portion 16 which extends beyond the beam from a point at which the spike is physically connected to the beam, such as by a welded or soldered joint 18. At a diametrically opposite point the working end 20 of the spike exits the beam through an opening 22 which is of a diameter greater than the spike diameter D. The working end 20 terminates as a sharp tip 23 and has a barb 25 extending therefrom.

The spike 14 lies in a plane in which the circular beam is disposed, namely in the plane in which the cross section of the beam is circular. As shown, the spike 14 can be viewed as bisecting the circular beam 12 into two halves. A strain gauge 30 is bonded to the beam, preferably at a midpoint between joint 18 and opening 22. The strain gauge is connected by leads 31 and 32 to an appropriate recorder 35.

Since the spike diameter is less than the diameter of opening 22, the beam portion around the opening is free to move relative to the spike. When a force is applied to the beam portion around opening 22 in a direction, as represented by arrow 36, the circular beam becomes partially deformed with its curvature increasing, therefore increasing the tension (or strain) to which the beam is subjected, from its minimal tension when no force is applied. The increased tension is sensed by the strain gauge 30, whose output changes and is recorded by recorder 35.

Figure 2:
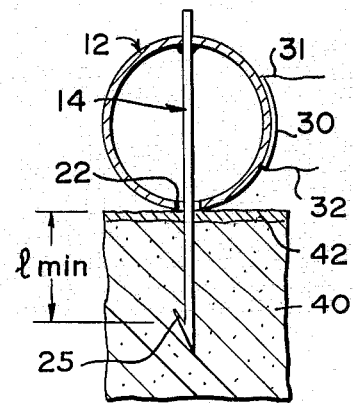
FIGS. 2 and 3 are cross sectional diagrams useful in explaining the manner in which the transducer of FIG. 1 is used.

The manner in which the novel transducer is used to measure changes in myocardium thickness will now be described in connection with FIG. 2. As shown therein, the working end 20 of the spike 14 is inserted into the myocardium 40 through the epicardium 42, which is the outer surface or wall of the myocardium 40, until the beam 12 is in intimate contact with the epicardium, so that a minimal beam-deforming force is applied by the myocardium to the beam. The spike is inserted so that it and the beam 12 are in a plane which is essentially perpendicular to the epicardium at the point of insertion. In practice, the insertion is performed during the heart expansion in the cardiac cycle when the myocardium thickness is a minimum. The minimal force which the myocardium applies to the beam is indicated by the recorder output. Based on prior calibration of the transducer the effective depth of insertion which is determined from the barb 25 to the slightly deformed beam, which is in contact with the epicardium, is easily determined.

Figure 3:
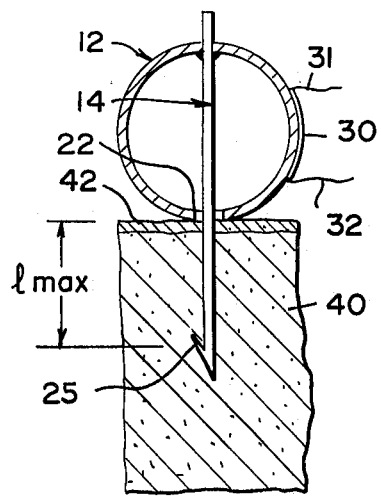

As the heart starts to contract, the myocardium thickness increases and therefore the beam is subjected to a greater deformation force. This force increases the beam curvature and therefore the beam tension, sensed by strain gauge 30, which provides a greater output, recorded by recorder 35. FIG. 3 is a diagram similar to FIG. 2, except that in it the myocardium thickness is greater than that in FIG. 2 and therefore the beam deformation is greater and the recorded output is therefore greater.

Figure 4:
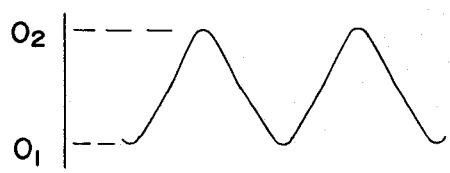
FIG. 4 is a waveform diagram of an output of a recorder used to indicate changes in myocardium wall thickness as sensed by the novel transducer.

FIG. 4 to which reference is made is a typical waveform of the output of recorder 35 where the minimum output $O_1$ represents the output when the transducer is inserted and the myocardium thickness is a minimum, at maximum heart expansion. The maximum output $O_2$ represents the recorder output when the myocardium thickness is at a maximum, at maximum heart contraction. From prior calibration the outputs $O_1$ and $O_2$ can be related to the initial depth of insertion, defined as $l_{min}$ and designated in FIG. 2, and to the expanded depth due to the increase in myocardium thickness, designated as $l_{max}$ in FIG. 3. From the two values $l_{min}$ and $l_{max}$ the change in myocardium thickness for the depth of insertion, $l_{min}$ can be determined. More importantly, the relative change in myocardium thickness for $l_{min}$ can be determined from the expression $(l_{max} - l_{min})/l_{min}$.

It should be emphasized that the transducer of the present invention need not be inserted through the entire myocardium, which is the case with prior art transducers. Furthermore, the present transducer, despite the small barb 25, can be extracted from one place in the myocardium and inserted in a different location without having to cut open the myocardium which would result in the death of the experimentally used animal. The transducer is very small and light and the beam 12 is of very high compliance so that the transducer does not load the heart and thereby interfere with the myocardium wall thickness changes as the heart contracts and expands. In one embodiment actually reduced to practice the beam 12 consisted of a stainless steel strip about 0.100 inch inch wide and 0.002 inch thick whose opposite ends were joined together to form the circular beam while the spike 14 was a stainless steel rod about 1 inch long and of a diameter of about 0.028 inch. The entire transducer weighed on the order of 0.050 gram.

Another advantage of the transducer is the ease with which it is insertable into the myocardium. Generally, an insertion tool is placed around top portion 16 of the spike 14 for transducer insertion. After the minimal loading of the beam 12 is achieved at minimum myocardium thickness the tool is removed and the transducer remains in position. With two heart beats per second the transducer can be inserted in a few seconds even by technicians of limited skill, while prior art transducers require insertion time of up to 30 minutes by skilled technicians.

Figure 5:
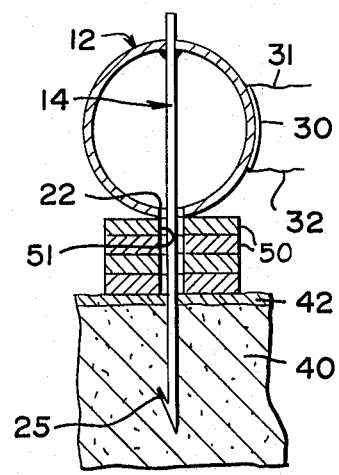
FIG. 5 is a cross sectional sectional diagram showing the novel transducer with spacers used to initial depth of insertion.

Another very important feature of the novel transducer of the present invention is that unlike prior art transducers, which must be inserted through the entire myocardium thickness, the present transducer can be inserted at different depths. This can be achieved by using spacers which may be placed around the working portion 20 of spike 14, as shown in FIG. 5, in which the spacers are designated by numerals 50. Each spacer has an opening 51 of a diameter which is greater than the spike diameter. Clearly, by varying the number of spacers the initial depth of insertion into the myocardium can be varied.

This capability is particularly important if the relative change of myocardium thickness is not uniform but rather varies as a function of depth. This point may best be explained in connection with numerical examples. Let it be assumed that the minimum myocardium thickness is 10mm and that the maximum thickness is 13mm and that the relative change is uniform across the myocardium thickness. It is clear that if the transducer is inserted through the entire thickness the minimum and maximum readings would correspond to thickness of 10mm and 13mm for a relative change for a depth of 10mm of $(13-10)/10 = 3/10 = 30\%$. Similarly, since the relative change is uniform if the transducer is inserted only to a depth of 5mm the minimum and maximum readings would correspond to 5mm and 6.5mm for a relative change of $(6.5-5)/5 = 1.5/5 = 30\%$. Thus, if the relative change in thickness is uniform the initial depth of penetration is not important, since similar results will be obtained regardless of penetration depth.

On the other hand, let it be assumed that most of the myocardium thickness change is due to the muscles closer to the epicardium. Let it further be assumed that the muscles to a depth of 2.5mm from the epicardium expand by 1.2mm, those muscles between 2.5mm and 5mm expand by 0.8mm, those muscles between 5mm and 7.5mm expand by 0.6mm and those between 7.5mm and 10mm expand by only 0.4mm. Using these assumed values it is clear that after the transducer is inserted to a depth of 10mm, the total myocardium thickness increase is $0.4 + 0.6 + 0.8 + 1.2 = 3$mm for a relative change of $(13-10)/10 = 3/10 = 30\%$ for a depth of insertion of 10mm. However, when the transducer is only inserted to a depth of 7.5mm the increase in thickness is $0.6 + 0.8 + 1.2 = 2.6$mm for a relative change $2.6/7.5 = 34.6\%$. At a depth of insertion of 5mm the increase in thickness is 0.8 + 1.2 = 2mm for a relative change 2/5 = 40%, and when the transducer is only inserted to a depth of 2.5mm the thickness increase is 1.2mm for a relative change 1.2/2.5 = 48%.

It should thus be appreciated that with the novel transducer of the present invention which can be inserted at different depths by use of the spacers 50 a profile of relative change in myocardium thickness, as a function of depth can be obtained. This is not possible with the prior art transducers which penetrate the entire myocardium thickness and therefore can only measure the change in the thickness as a function of the total myocardium thickness.

Figure 6:
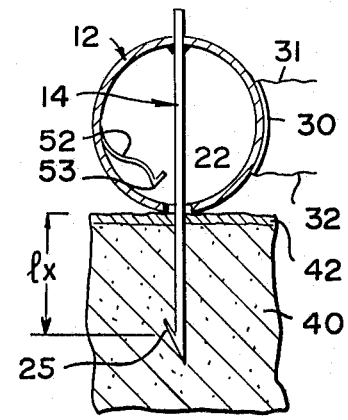
FIG. 6 is a cross sectional diagram of another embodiment of the transducer.
Figure 7:
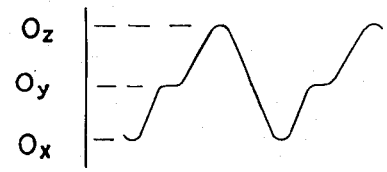
FIG. 7 is a waveform diagram of the output of a recorder when the transducer shown in FIG. 6 is used.

In another embodiment of the invention, as shown in FIG. 6, a calibrating tine 52 with a downwardly pointing tip 53 is attached to and within the circular beam 12. The distance from the barb 25 to tine 53 is known to a high degree of accuracy. The transducer is inserted, as hereinbefore described, so that the beam is slightly deformed when the myocardium is of minimum thickness. The corresponding recorder output is designated as $O_x$ in FIG. 7. As the myocardium thickness increases the beam is deformed until it touches the tip 53 of the calibrating tine 52. As a result a slight inflection occurs in the recorder output as represented by output $O_y$. At this point the myocardium thickness from barb 25 is known very precisely since it corresponds to the precisely known distance between the barb 25 and tip 53 of calibrating tine 52. Thereafter the force which is applied by the expanding myocardium continues to deform the beam as well as push the tine 52 upwardly until maximum myocardium thickness is reached when the recorder output is $O_z$.

From prior transducer calibration the increase in myocardium thicknesses corresponding to the differences between outputs $O_z$ and $O_y$ and $O_y$ and $O_x$ are known. Therefore, the actual depth of initial penetration, designated in FIG. 6 by $l_x$, and the maximum myocardium thickness from barb 25 to the epicardium at maximum heart compression are easily determinable. For example, let it be assumed that the known distance between the tip 53 and barb 25 is exactly 10mm and that from prior calibrations the difference between outputs $O_y$ and $O_x$ corresponds to a thickness of 1.0mm and the difference between $O_y$ and $O_z$ corresponds to a thickness change of 1.5mm. It is therefore easily seen that the initial depth of penetration is 10 − 1.0 = 9mm and that the final myocardium thickness is 10 + 1.5 = 11.5mm. Thus, the thickness change is 11.5 − 9 = 2.5mm and the relative change in thickness for a depth of 9mm is (11.5 − 9)/9 = 2.5/9 = 27.7%.

Although the invention was invented with the primary purpose for use in detecting changes in myocardium thickness, it should be appreciated that it is not intended to be limited thereto. It can be used to measure changes in thickness of any material in which the spike can be inserted through an exposed surface of said material.

Also, hereinbefore the beam 12 has been described as circular, which was assumed to be its initial shape prior to insertion into the myocardium. It should however be appreciated that the invention is not intended to be limited thereto. For example, the initial shape of the beam may be oval, or polygon-like. The important aspect of the beam 12 is that it is shaped to form a closed loop, and that the transducer spike 14 is physically connected to the beam at one point (joint 18) while passing through an opening 22 in the beam at a substantially diametrically opposite point so that the beam portion around the opening is free to move, i.e., be displaced relative the spike when a beam-deforming force is applied thereto. The beam deformation results in a change in tension which is sensed by the strain gauge 30 which is bonded to the beam and whose output changes as a function of changes in beam tension. If desired a second strain gauge may be bonded to the beam at a different location and the outputs of the two gauges may be compared or averaged.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A transducer for measuring changes in thickness of a material, comprising:
   a closed loop shaped beam of high elastic compliance, said beam defining an opening therein;
   an elongated rod-shaped spike of a diameter less than the diameter of said opening, said spike having a portion extending into said loop through said opening and being connected to said beam at a point substantially opposite said opening, said spike further including a working portion extending outwardly from said opening and terminating in a tapered end, the working portion of said spike being adapted to be inserted in a material, whose thickness change is to be measured, through an exposed surface of said material, to a depth so that said exposed surface is in intimate contact with the portion of the beam around said opening, with said material applying a minimal beam-deforming force to said beam; and
   strain gauge means including a strain gauge bonded to said beam between said opening and the point at which said spike is connected to said beam for measuring changes in the beam strain as a function of the beam-deforming forces applied thereto.

2. The transducer as described in claim 1 wherein said beam is of a width definable as D, with the diameter of said opening being less than D, and the spike being in the plane in which said beam is disposed which is perpendicular to the beam width direction, the portion of the spike extending into said beam effectively bisecting said beam into two substantially equal halves.

3. The transducer as described in claim 2 wherein said spike further includes a top portion extending outwardly from said beam from the point at which said spike is connected to said beam, said spike further including a barb adjacent the tapered end of the working portion thereof.

4. The transducer as described in claim 2 wherein said transducer further includes a calibrating flexible tine extending in said beam and having one end connected to the beam and an opposite free end adjacent to and spaced apart from the beam portion surrounding said opening.

5. The transducer as described in claim 2 wherein said beam is substantially circular in the absence of beam-deforming forces applied to the portion thereof surrounding said opening.

6. The transducer as described in claim 5 wherein said spike further includes a top portion extending outwardly from said beam from the point at which said spike is connected to said beam.

7. The transducer as described in claim 2 wherein said working portion of said spike includes a barb adjacent the tapered end thereof.

8. The transducer as described in claim 7 wherein said beam is substantially circular in the absence of beam-deforming forces applied to the portion thereof surrounding said opening and said spike further includes a top portion extending outwardly from said beam from the point at which said spike is connected to said beam.

9. The transducer as described in claim 8 wherein said transducer further includes a calibrating flexible tine extending in said beam and having one end connected to the beam and an opposite free end adjacent to and spaced apart from the beam portion surrounding said opening.

10. A method of measuring changes in wall thickness of the myocardium of a living subject, the steps comprising:
providing a transducer which essentially consists of a substantially circular beam of high elastic compliance, said beam defining an opening, a rod-shaped spike having a portion thereof extending into said beam through said opening and being connected to said beam at a point substantially opposite said opening, said spike having a working portion extending outwardly from said beam through said opening and terminating in a sharpened tip, and at least one strain gauge bonded to said beam for sensing changes in beam strain as a function of beam deforming forces applied to the portion of the beam about said opening;
inserting the working portion of said spike into the myocardium through the epicardium thereof to a depth whereby said myocardium applies a minimal beam deforming force to said beam when the myocardium is substantially at minimum thickness, and as said myocardium thickness increases due to heart contraction the beam deforming force increases resulting in increased strain on said beam sensed by said strain gauge; and
measuring changes in the output of said strain gauge.

* * * * *